United States Patent
Pan et al.

(10) Patent No.: US 9,788,749 B2
(45) Date of Patent: Oct. 17, 2017

(54) SYSTEM AND METHOD FOR DETECTING BONE DEFECTS

(71) Applicant: National Central University, Jhongli, Taoyuan County (TW)

(72) Inventors: Min-Chun Pan, Ping-Jen (TW); Tai-Shin Chia, Selangor (MY); Chin-Sung Chen, Taipei (TW); Shyh-Yuan Lee, Taipei (TW)

(73) Assignee: NATIONAL CENTRAL UNIVERSITY, Jhongli, Taoyuan County (TW)

( * ) Notice: Subject to any disclaimer, the term of this patent is extended or adjusted under 35 U.S.C. 154(b) by 847 days.

(21) Appl. No.: 14/200,345

(22) Filed: Mar. 7, 2014

(65) Prior Publication Data

US 2015/0150474 A1 Jun. 4, 2015

(30) Foreign Application Priority Data

Dec. 2, 2013 (TW) .............................. 102144087 A

(51) Int. Cl.
*A61B 5/05* (2006.01)
*A61B 5/00* (2006.01)
*A61C 8/00* (2006.01)

(52) U.S. Cl.
CPC .............. *A61B 5/05* (2013.01); *A61B 5/0051* (2013.01); *A61B 5/4547* (2013.01); *A61B 5/7278* (2013.01); *A61B 5/682* (2013.01); *A61B 5/686* (2013.01); *A61B 5/7203* (2013.01); *A61C 8/00* (2013.01)

(58) Field of Classification Search
CPC ....... A61B 5/0051; A61B 5/05; A61B 5/4547; A61B 5/682; A61B 5/686; A61B 5/7203; A61B 5/7278; A61C 8/00
See application file for complete search history.

(56) References Cited

U.S. PATENT DOCUMENTS 5,392,779 A 2/1995 Meredith et al.
5,518,008 A 5/1996 Cucchiaro et al.
(Continued)

FOREIGN PATENT DOCUMENTS

TW 476633 2/2002
TW 483750 4/2002
(Continued)

OTHER PUBLICATIONS

Meredith, N., Alleyne, D. and Cawley, P.,"Quantitative Determination of the Stability of the Implant-Tissue Interface Using Resonance Frequency Analysis," Clinical Oral Implants Research. vol. 7(3), pp. 261-267 (1996).

(Continued)

*Primary Examiner* — Ruth S Smith
(74) *Attorney, Agent, or Firm* — McClure, Qualey & Rodack, LLP

(57) ABSTRACT

A system for detecting bone defects includes a dental implant contacting member, at least one electromagnetic source, at least one first magnetic field detecting device, at least one second magnetic field detecting device and a computing device. The dental implant contacting member has a magnetic body. The electromagnetic source is used to generate a variable magnetic field to vibrate the magnetic body. The first magnetic field detecting device is used to detect a magnetic field of the magnetic body and the variable magnetic field, so as to generate first detected data. The second magnetic field detecting device is used to detect the variable magnetic field, so as to generate second detected data. The computing device is used to obtain vibration data based on the difference between the first detected data and the second detected data.

12 Claims, 10 Drawing Sheets

(56) References Cited

U.S. PATENT DOCUMENTS

| | | |
|---|---|---|
| 7,147,467 B2 | 12/2006 | Shoji et al. |
| 8,391,958 B2 | 3/2013 | Cawley et al. |
| 2002/0143268 A1 | 10/2002 | Meredith et al. |
| 2002/0177790 A1 | 11/2002 | Meredith et al. |
| 2009/0092945 A1 | 4/2009 | Wu et al. |
| 2011/0200965 A1* | 8/2011 | Petersson ............... A61C 19/04 433/172 |

FOREIGN PATENT DOCUMENTS

| | | |
|---|---|---|
| TW | 1238053 | 8/2005 |
| TW | 200631556 | 9/2006 |

OTHER PUBLICATIONS

M. Yamane, M. Yamaoka, M. Hayashi, I. Furutoyo, N. Komori, and B. Ogiso. "Measuring tooth mobility with a no-contact vibration device," Journal of periodontal research. vol. 43, pp. 84-89, 2008.

M. Hayashi, C. Kobayashi, H. Ogata, M. Yamaoka, and B. Ogiso, "A no-contact vibration device for measuring implant stability," Clinical Oral Implants Research. vol. 21, pp. 931-936, 2010.

K. A. Lilienkamp, "Low-cost magnetic levitation project kits for teaching feedback system design," presented at the IEEE, Boston, Massachusetts, 2004, pp. 1308-1313.

L. Williams, "Electromagnetic Levitation," undergraduate, Department of Electrical Engineering, University of Cape Town, 2005.

\* cited by examiner

SYSTEM AND METHOD FOR DETECTING BONE DEFECTS

RELATED APPLICATIONS

This application claims priority to Taiwanese Application Serial Number 102144087, filed Dec. 2, 2013, which is herein incorporated by reference.

BACKGROUND

Technical Field

Embodiments of the present disclosure relate to a detecting system. More particularly, embodiments of the present disclosure relate to a system for detecting irregular bone defects after dental implantation surgery.

Description of Related Art

Dental implantations have become a common dental surgical technique. Currently, there are two types of dental implantation including immediate implantation and two-stage implantation in accordance with the dental implant type and surgical method. In the immediate implantation, a portion of the dental implant is still exposed out of the gingiva after the dental implant is implanted in the alveolus bone, and thereafter a dental crown is mounted on the dental implant. In the two-stage implantation, the dental implant is entirely covered in the gingiva, and the dental crown is installed by creating an incision on the gingiva after osseointegration. As a result, in the case of two-stage implantation, the external stimuli to the dental implant and the alveolus bone during the period of osseointegration can be alleviated, and thus the probability of infection can be reduced, so that the dental implant can be combined with the alveolus bone more stably.

When the dental implant is implanted, the bone newly formed can tightly contact the dental implant when the bone tissue is healed, such that good stability between the dental implant and the bone tissue can be achieved. This process is referred to as osseointegration. Generally speaking, it takes about six months for the alveolus bone of the palate to reach an acceptable level of osseointegration, and about three or four months for the alveolus bone of the mandible.

The stability of the dental implant plays a very important role in the success of implantation. If better osseointegration takes place, higher stability of the dental implant can be achieved, and thus the implantation surgery can have a higher success rate. Therefore, it is one of critical steps for evaluating the stability of a dental implant during and after implantation surgery.

SUMMARY

In view of the foregoing, one aspect of the present disclosure is to facilitate the evaluation of the stability of a dental implant.

In accordance with one embodiment of the present disclosure, a system for detecting bone defects includes a dental implant contacting member, at least one electromagnetic source, at least one first magnetic field detecting device, at least one second magnetic field detecting device and at least one computing device. The dental implant contacting member has a magnetic body. The electromagnetic source is used for generating a variable magnetic field to vibrate the magnetic body. The first magnetic field detecting device is used for detecting a magnetic field of the magnetic body and the variable magnetic field, so as to generate first detected data. The second magnetic field detecting device is used for detecting the variable magnetic field, so as to generate second detected data. The computing device is used for obtaining vibration data based on a difference between the first detected data and the second detected data.

In accordance with another embodiment of the present disclosure, an apparatus for detecting bone defects includes at least one detector and at least one computing device. The detector includes an electromagnetic source, a first magnetic field detecting device and a second magnetic field detecting device. The electromagnetic source is used for generating a variable magnetic field to vibrate a dental implant contacting member. The first magnetic field detecting device is used for detecting a magnetic field of the dental implant contacting member and the variable magnetic field, so as to generate first detected data. The second magnetic field detecting device is used for detecting the variable magnetic field, so as to generate second detected data. The computing device is used for obtaining vibration data based on a difference between the first detected data and the second detected data.

In the foregoing embodiments, the first magnetic field detecting device and the second magnetic field detecting device respectively obtain the first detected data and the second detected data. The data with respect to variable magnetic field generated from the electromagnetic source can be removed by obtaining the difference between the first detected data and the second detected data, so that the data with respect to the magnetic field variation due to the vibration of the dental implant contacting member can be obtained, so as to obtain the vibration data of the dental implant contacting member and to facilitate evaluation of the stability of the dental implant.

In accordance with another embodiment of the present disclosure, a method for detecting bone defects includes the following steps. A detector is provided, which has an electromagnetic source and at least one magnetic field detecting device disposed on the electromagnetic source. A variable magnetic field generated from the electromagnetic source is detected by the magnetic field detecting apparatus, so as to obtain first detected data. A magnetic body of a dental implant contacting member is vibrated by the variable magnetic field. The variable magnetic field and a magnetic field of the magnetic body are detected by the magnetic field detecting device to obtain second detected data. A vibration data is obtained based on a difference between the third detected data and the fourth detected data.

It is to be understood that both the foregoing general description and the following detailed description are by examples, and are intended to provide further explanation of the disclosure as claimed.

BRIEF DESCRIPTION OF THE DRAWINGS

The disclosure can be more fully understood by reading the following detailed description of the embodiment, with reference made to the accompanying drawings as follows.

DETAILED DESCRIPTION

Figure 1:
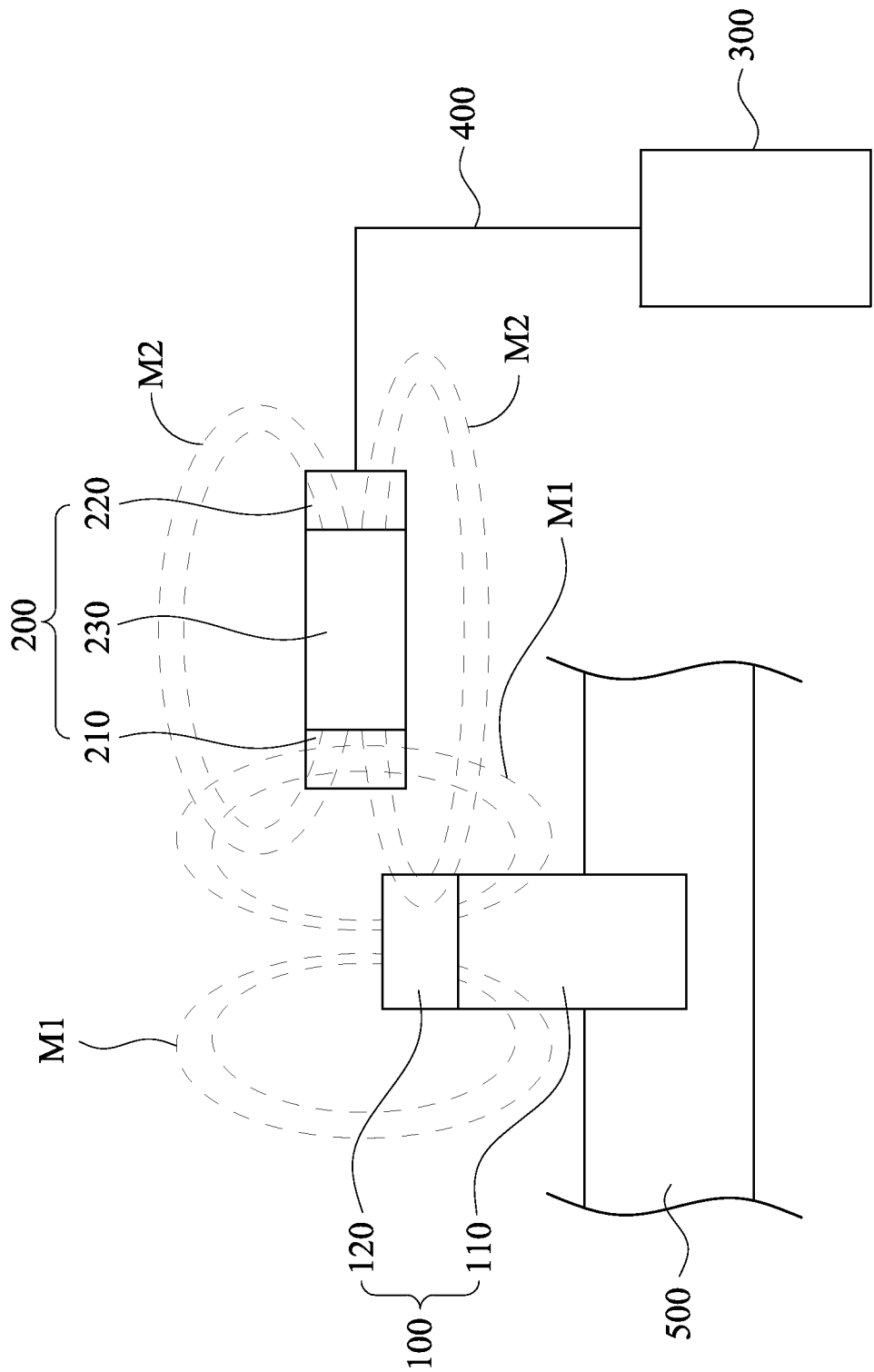
FIG. 1 is a schematic view of a system for detecting bone defects in accordance with one embodiment of the present disclosure.

Reference will now be made in detail to the present embodiments of the disclosure, examples of which are illustrated in the accompanying drawings. Wherever possible, the same reference numbers are used in the drawings and the description to refer to the same or like parts.

FIG. 1 is a schematic view of a system for detecting bone defects in accordance with one embodiment of the present disclosure. As shown in FIG. 1, in this embodiment, the system includes a dental implant contacting member 100, a detector 200, a processing device 300 and a connection wire 400. The dental implant contacting member 100 is in physical contact with the dental implant 500, and includes a magnetic body 120. The magnetic body 120 has a magnetic field M1. The connection wire 400 is electrically connected to the detector 200 and the processing device 300. The detector 200 includes a first magnetic field detecting device 210, a second magnetic field detecting device 220 and an electromagnetic source 230. During operation, the electromagnetic source 230 generates a variable magnetic field M2 to vibrate the magnetic body 120. The first magnetic field detecting device 210 detects the magnetic field M1 of the magnetic body 120 and the variable magnetic field M2 generated from the electromagnetic source 230, so as to generate first detected data. The second magnetic field detecting device 220 detects the variable magnetic field M2, so as to generate second detected data. The processing device 300 obtains a vibration data based on a difference between the first detected data and the second detected data.

In detail, the magnetic body 120 is positioned in the variable magnetic field M2, and thus can be moved by the attractive force or the repulsive force between the magnetic field M1 and the variable magnetic field M2. The intensity, the polarity, or any combination of the variable magnetic field M2 is variable. Therefore, when the intensity, the polarity, or both of the variable magnetic field M2 varies, the magnetic body 120 vibrates due to the change regarding the variable magnetic field M2, such that the intensity of magnetic field M1 detected by the first magnetic field detecting device 210 varies. The higher the amplitude of the vibration of the magnetic body 120 is, the greater the detected intensity variation of the magnetic field M1 is. The higher the frequency of the vibration of the magnetic body 120 is, the higher the frequency of the detected intensity variation of the magnetic field M1 is. In other words, the detected intensity variation of the magnetic field M1 is in positive correlation with the amplitude of the vibration of the magnetic body 120, and the frequency of the detected intensity variation of the magnetic field M1 is in positive correlation with the frequency of the vibration of the magnetic body 120 as well. As a result, the vibration data of the magnetic body 120, such as the amplitude and the frequency of vibration, can be obtained based on the detected intensity variation of the magnetic field M1. Moreover, because the first detected data is the sum of intensities of the magnetic field M1 and the variable magnetic field M2, and the second detected data is the intensity of the variable magnetic field M2, the difference between the first detected data and the second detected data is the intensity of the magnetic field M1.

Because the dental implant contacting member 100 is in physical contact with the dental implant 500, the dental implant 500 vibrates along with the dental implant contacting member 100. As such, the stability of the dental implant 500 can be evaluated based on the vibration data of the dental implant contacting member 100. For example, the resonance frequencies of the dental implant contacting member 100 can be respectively obtained at different dates after the dental implant 500 is implanted. When the obtained resonance frequencies are stable or reach values within an expected range, it can be determined that the dental implant 500 is firmly combined with the new bone tissue.

In some embodiments, as shown in FIG. 1, the first magnetic field detecting device 210 can be positioned between the dental implant contacting member 100 and the electromagnetic source 230. In other words, the first magnetic field detecting device 210 and the electromagnetic source 230 are positioned on the same side of the dental implant contacting member 100, rather than on opposite sides of the dental implant contacting member 100. In such a configuration, the size of the detector 200 can be reduced, so as to facilitate operation.

In some embodiments, the second magnetic field detecting device 220 is positioned out of a range of the magnetic field M1 of the magnetic body 120 of the dental implant contacting member 100. In other words, the second magnetic field detecting device 220 is positioned on the area through which the magnetic field lines of the magnetic field M1 do not pass, so as to prevent the magnetic field M1 of the magnetic body 120 from being detected. Further, the second magnetic field detecting device 220 is positioned in the variable magnetic field M2 generated from the electromagnetic source 230, so as to detect the variable magnetic field M2. The first magnetic field detecting device 210 is positioned in the magnetic field M1 and the variable magnetic field M2, so as to detect the magnetic field M1 and the variable magnetic field M2.

In some embodiments, as shown in FIG. 1, the first magnetic field detecting device 210 and the second magnetic field detecting device 220 are respectively positioned on opposite ends of the electromagnetic source 230. In particular, the first magnetic field detecting device 210 can be positioned on one end of the electromagnetic source 230 that is closest to the magnetic body 120, and the second magnetic field detecting device 220 can be positioned on another end of the electromagnetic source 230 that is farthest away from the magnetic body 120. In such a configuration, the first magnetic field detecting device 210 can be closer to the magnetic body 120 than the second magnetic field detecting device 220 is, so that the first magnetic field detecting device 210 can be positioned in the magnetic field M1 when the second magnetic field detecting device 220 is positioned out of the range of the magnetic field M1.

In some embodiments, as shown in FIG. 1, the dental implant contacting member 100 includes a cantilever 110. The cantilever 110 is partially inserted into the dental implant 500 and is partially exposed out of the dental implant 500. The magnetic body 120 can be disposed on the cantilever 110. As such, when the magnetic body 120 vibrates, the cantilever 110 and the dental implant 500 also vibrate. For example, the magnetic body 120 can be disposed on the free end of the cantilever 110, namely, on the end of the cantilever 110 farthest away from the dental implant 500.

Figure 2:
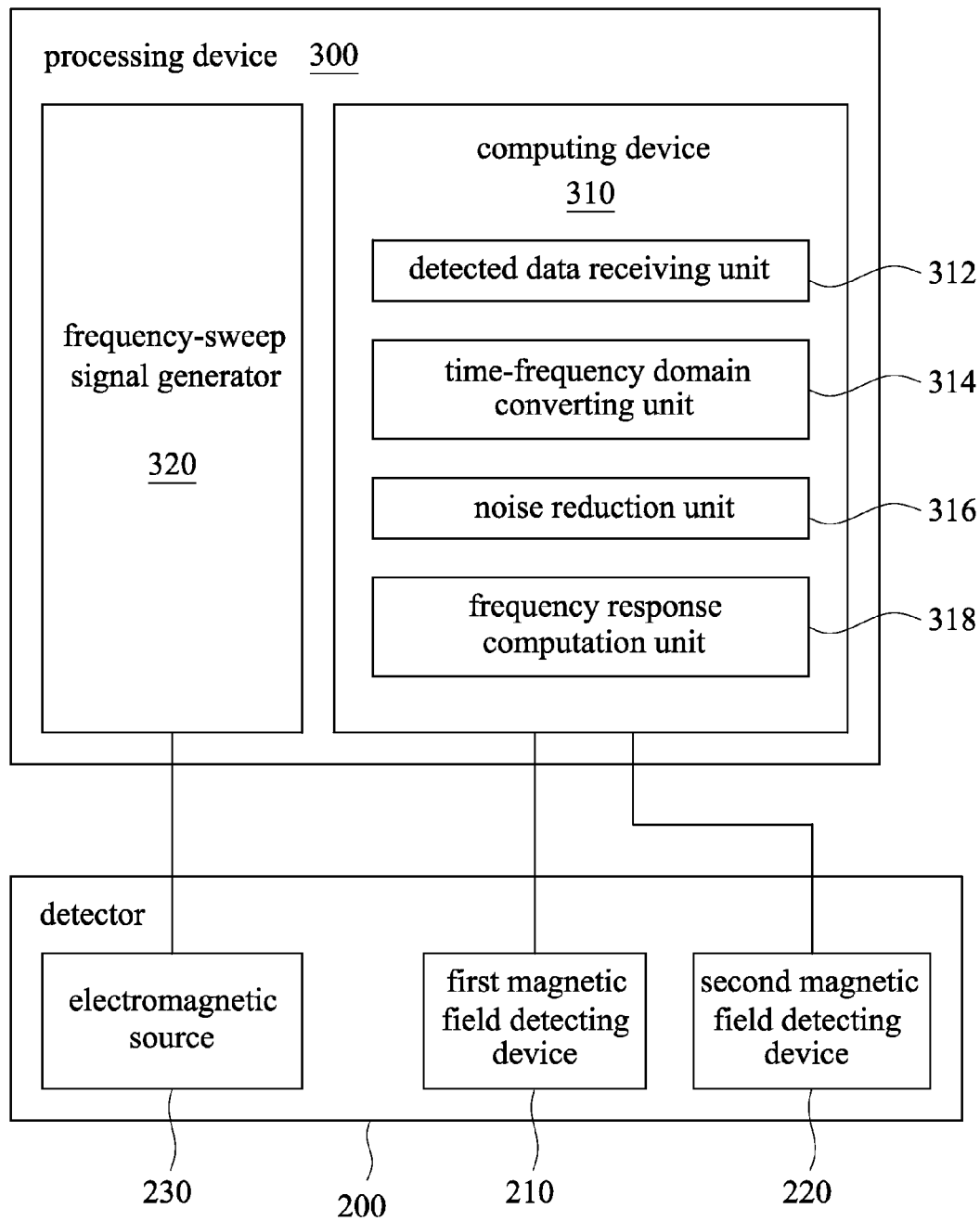
FIG. 2 is a block diagram of the system in accordance with one embodiment of the present disclosure.

FIG. 2 is a block diagram of the system in accordance with one embodiment of the present disclosure. As shown in FIG. 2, the processing device 300 includes a computing device 310 and a frequency-sweep signal generator 320. The frequency-sweep signal generator 320 can be electrically connected to the electromagnetic source 230 of the detector 200, so as to control the variable magnetic field M2 (See FIG. 1) by using a frequency-sweep signal. For example, the frequency-sweep signal generator 320 provides an AC (Alternating Current) signal having a time-variant frequency, so that the frequency of the variable magnetic field M2 varies with time, and the frequency of vibration of the dental implant contacting member 100 (See FIG. 1) varies with time as well. As a result, the amplitude of vibration of the dental implant contacting member 100 at different frequencies can be detected, so as to obtain the resonance frequency. The frequency of the variable magnetic field M2 is the number of occurrences of polarity alternation of the variable magnetic field M2 per unit time.

In some embodiments, as shown in FIG. 2, the computing device 310 can be electrically connected to the first magnetic field detecting device 210 and the second magnetic field detecting device 220, so as to obtain the vibration data of the dental implant contacting member 100 (See FIG. 1) based on the difference between the first detected data and the second detected data. For example, in some embodiments, the computing device 310 includes a detected data receiving unit 312, a time-frequency domain converting unit 314, a noise reduction unit 316 and a frequency response computation unit 318. The detected data receiving unit 312 receives the first detected data detected by the first magnetic field detecting device 210 and the second detected data detected by the second magnetic field detecting device 220.

In some embodiments, the first detected data and the second detected data are time-domain data. For example, the first detected data is the sum of intensities of the magnetic field M1 and the variable magnetic field M2 at different time, and the second detected data is the intensity of the variable magnetic field M2 at different time. The time-frequency domain converting unit 314 converts the first detected data and the second detected data to first frequency-domain data and second frequency-domain data. For example, the time-frequency domain converting unit 314 performs Fourier transform to the first detected data and the second detected data, so as to generate the first frequency-domain data and the second frequency-domain data, in which the first frequency-domain data is the sum of intensities of the magnetic field M1 and the variable magnetic M2 at different frequencies, and the second frequency-domain data is the intensity of the variable magnetic field M2 at different frequencies.

There may be some noises existing in the frequency-domain data, and therefore, in some embodiments, the noise reduction unit 316 can be used to lower the noises in the first frequency-domain data and the second frequency-domain data. For example, the noise reduction unit 316 can perform RMS (root-mean square) calculation with respect to the intensities of the magnetic fields at every N frequencies, so as to obtain the RMS value of the intensities of the magnetic fields at every N frequencies. This RMS value is used as the intensity of the magnetic field at those N frequencies, thereby reducing the noises.

The frequency response computation unit 318 obtains a frequency response function of the dental implant contacting member 100 based on the first frequency-domain data and the second frequency-domain data, so as to obtain the resonance frequency of the dental implant contacting member 100. For example, the frequency response computation unit 318 can perform calculation with respect to the first frequency-domain data and the second frequency-domain data, such as dividing the first frequency-domain data by the second frequency-domain data. As such, the intensity variation of the magnetic field generated from the electromagnetic source 230 can be eliminated, thereby obtaining the frequency response function of the dental implant contacting member 100 (See FIG. 1) and obtaining the vibration data, such as the frequency and the amplitude of vibration. For example, the frequency response computation unit 318 can obtain the intensity variation of the magnetic field M1 of the magnetic body 120 of the dental implant contacting member 100, thereby obtaining the vibration data of the dental implant contacting member 100, which includes the vibration response.

Figure 3:
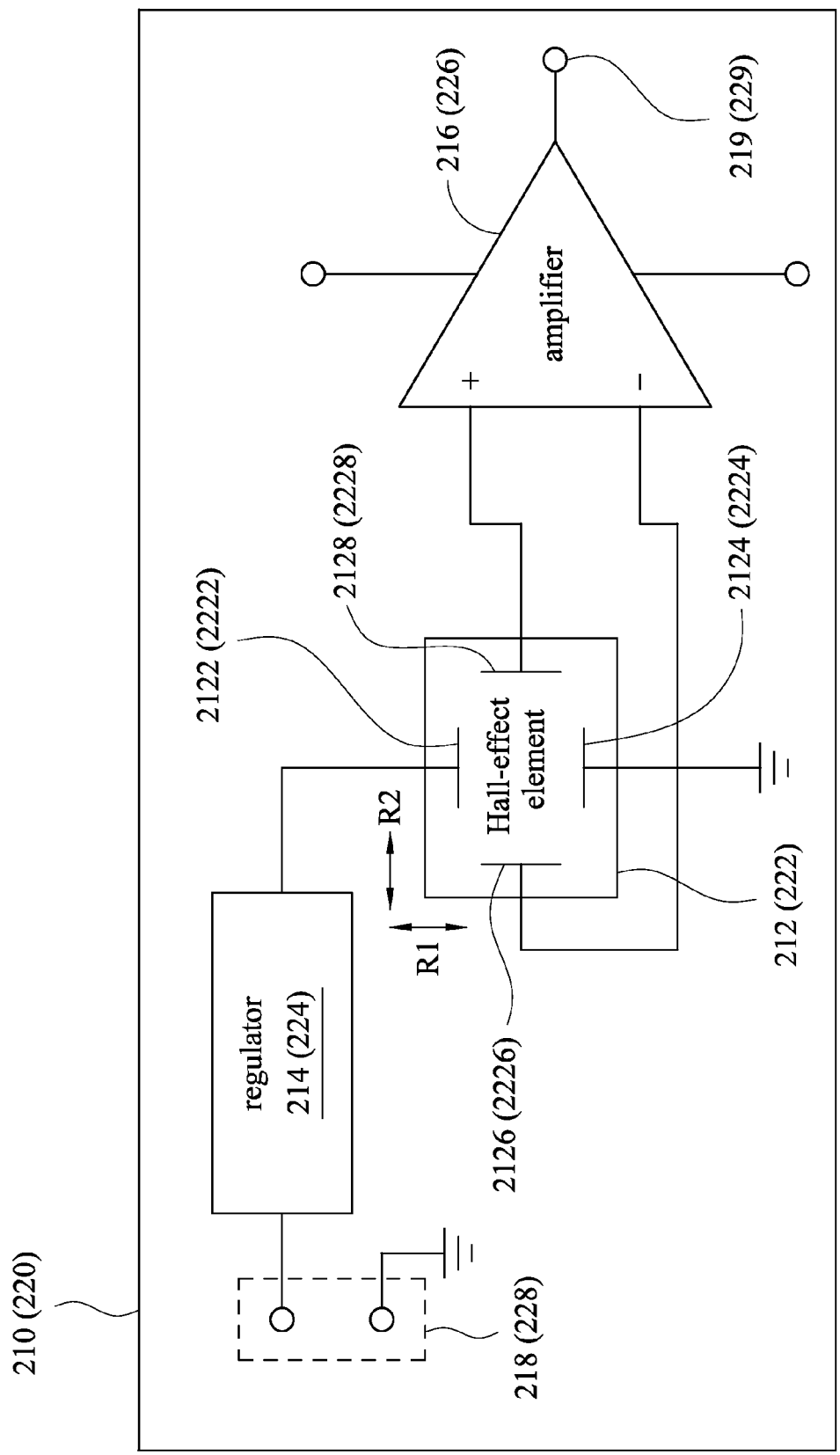
FIG. 3 is a circuit diagram of a first magnetic field detecting device or a second magnetic field detecting device in accordance with one embodiment of the present disclosure.

FIG. 3 is a circuit diagram of the first magnetic field detecting device 210 or the second magnetic field detecting device 220 in accordance with one embodiment of the present disclosure. In some embodiments, as shown in FIG. 3, the first magnetic field detecting device 210 can be a Hall-effect sensor that generates voltage in response to the magnetic field. For example, the first magnetic field detecting device 210 includes a Hall-effect element 212, a regulator 214, an amplifier 216, a voltage source 218 and an output terminal 219. The Hall-effect element 212 includes an upper connection terminal 2122, a lower connection terminal 2124, a left connection terminal 2126 and a right connection terminal 2128. The upper connection terminal 2122 and the lower connection terminal 2124 are arranged along the longitudinal direction R1, and the left connection terminal 2126 and the right connection terminal 2128 are arranged along the transversal direction R2. The longitudinal direction R1 and the transversal direction R2 can be substantially perpendicular to each other. The voltage source 218 is electrically connected to the upper connection terminal 2122 and the lower connection terminal 2124. The output terminal 219 is electrically connected to the left connection terminal 2126 and the right connection terminal 2128. It is understood that the relative terms in this context, such as "upper", "lower", "left" and "right", may be used herein to describe one element's relationship to another element as illustrated in the Figures. The relative terms are intended to encompass different orientations of the device in addition to the orientation depicted in the Figures. For example, the left connection terminal 2126 is not necessarily at the left side of the right connection terminal 2128.

When the voltage source 218 is turned on, the charges flow along the longitudinal direction R1 in the Hall-effect element 212. If the Hall-effect element 212 is not positioned in any magnetic field, there is no electric potential difference between the left connection terminal 2126 and the right connection terminal 2128. If the Hall-effect element 212 is positioned in the magnetic field, the magnetic field exerts Lorentz force on the charges and enables the charges to move along the transversal direction R2, such that the electric potential difference exists between the left connection terminal 2126 and the right connection terminal 2128. The higher the intensity of the magnetic field is, the greater the Lorentz force is, and thus, the electric potential difference, also referred to as a voltage, is higher. As a result, the intensity of the magnetic field in which the Hall-effect element 212 is positioned can be obtained based on the voltage measured at the output terminal 219.

In some embodiments, the regulator 214 can be electrically connected between the voltage source 218 and the Hall-effect element 212, so as to stabilize the voltage of the voltage source 218 provided to the Hall-effect element 212. In some embodiments, the amplifier 216 can be electrically connected between the Hall-effect element 212 and the output terminal 219, so as to amplify the electric potential difference between the left connection terminal 2126 and the right connection terminal 2128, thereby obtaining the intensity of the magnetic field in which the Hall-effect element 212 is positioned. In some embodiments, the amplifier 216 can be, but is not limited to, a differential amplifier.

In some embodiments, as shown in FIG. 3, the second magnetic field detecting device 220 can be a Hall-effect sensor as well, which generates a voltage in response to the magnetic field. For example, the second magnetic field detecting device 220 includes a Hall-effect element 222, a regulator 224, an amplifier 226, a voltage source 228 and an output terminal 229. The Hall-effect element 222 includes an upper connection terminal 2222, a lower connection terminal 2224, a left connection terminal 2226 and a right connection terminal 2228. The upper connection terminal 2222 and the lower connection terminal 2224 are arranged along the longitudinal direction R1, and the left connection terminal 2226 and the right connection terminal 2228 are arranged along the transversal direction R2. The voltage source 228 is electrically connected to the upper connection terminal 2222 and the lower connection terminal 2224. The output terminal 229 is electrically connected to the left connection terminal 2226 and the right connection terminal 2228.

When the voltage source 228 is turned on, the charges flow along the longitudinal direction R1 in the Hall-effect element 222. If the Hall-effect element 222 is not positioned in any magnetic field, there is no electric potential difference between the left connection terminal 2226 and the right connection terminal 2228. If the Hall-effect element 222 is positioned in the magnetic field, the magnetic field exerts Lorentz force on the charges and makes the charges to move along the transversal direction R2, such that the electric potential difference exists between the left connection terminal 2226 and the right connection terminal 2228. The higher the intensity of the magnetic field is, the greater the Lorentz force is, and thus, the electric potential difference, also referred to as a voltage, is higher. As a result, the intensity of the magnetic field on which the Hall-effect element 222 is positioned can be obtained based on the voltage measured at the output terminal 229.

In some embodiments, the regulator 224 can be electrically connected between the voltage source 228 and the Hall-effect element 222, so as to stabilize the voltage of the voltage source 228 provided to the Hall-effect element 222. In some embodiments, the amplifier 226 can be electrically connected between the Hall-effect element 222 and the output terminal 229, so as to amplify the electric potential difference between the left connection terminal 2226 and the right connection terminal 2228, thereby obtaining the intensity of the magnetic field in which the Hall-effect element 222 is positioned. In some embodiments, the amplifier 226 can be, but is not limited to, a differential amplifier.

Figure 4:
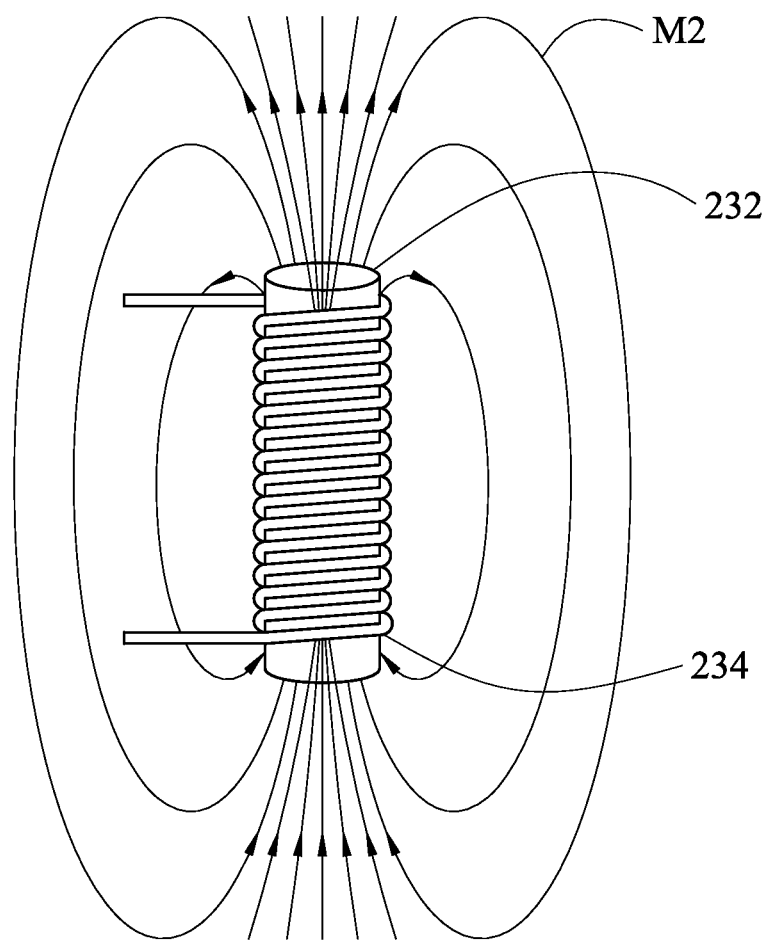
FIG. 4 is a 3D view of a electromagnetic source in accordance with one embodiment of the present disclosure.

FIG. 4 is a 3D view of the electromagnetic source 230 in accordance with one embodiment of the present disclosure. In some embodiments, as shown in FIG. 4, the electromagnetic source 230 includes an iron core 232 and a solenoid 234. The solenoid 234 is winded on the iron core 232. The solenoid 234 is electrically conductive. Preferably, the solenoid 234 can be provided with AC to generate the variable magnetic field M2. In some embodiments, the iron core 232 can be omitted.

Figure 5:
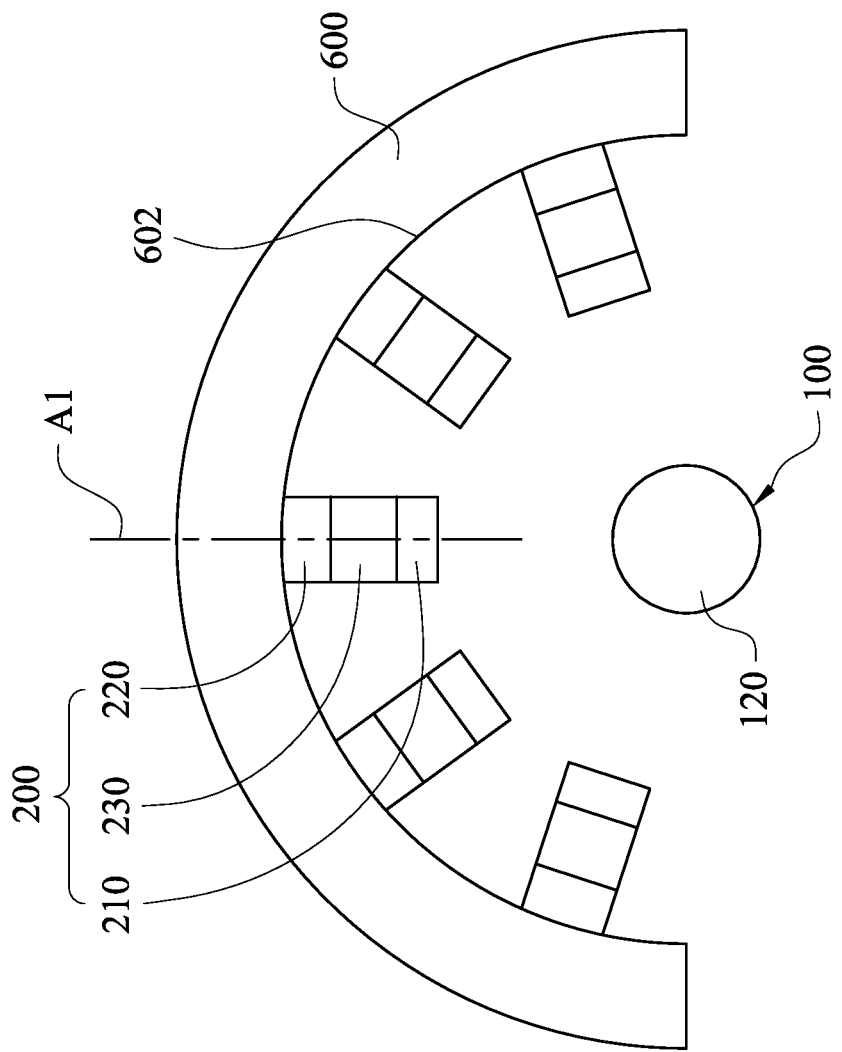
FIG. 5 is a schematic view of a system for detecting bone defects in accordance with another embodiment of the present disclosure.

FIG. 5 is a schematic view of the system for detecting bone defects in accordance with another embodiment of the present disclosure. The main difference between this embodiment and the foregoing embodiment is that this embodiment has plural detectors 200. Each detector 200 has an arrangement direction A1. The first magnetic field detecting device 210, the second magnetic field detecting device 220 and the electromagnetic source 230 are arranged along the arrangement direction A1 of the detector 200. The arrangement directions A1 of the detectors 200 cross to each other. In other words, the arrangement directions A1 of the detectors 200 are not parallel to each other. As a result, the detectors 200 can vibrate the dental implant contacting member 100 along different arrangement directions A1 to obtain the vibration data, thereby obtaining positions of bone defects accurately.

In some embodiments, as shown in FIG. 5, the apparatus for detecting bone defects includes a base 600. The base 600 has an inner surface 602. The detectors 200 are disposed on different positions of the inner surface 602. The inner surface 602 can be an arc surface, so as to make the arrangement directions A1 of the detectors 200 not parallel to each other.

Figure 6:
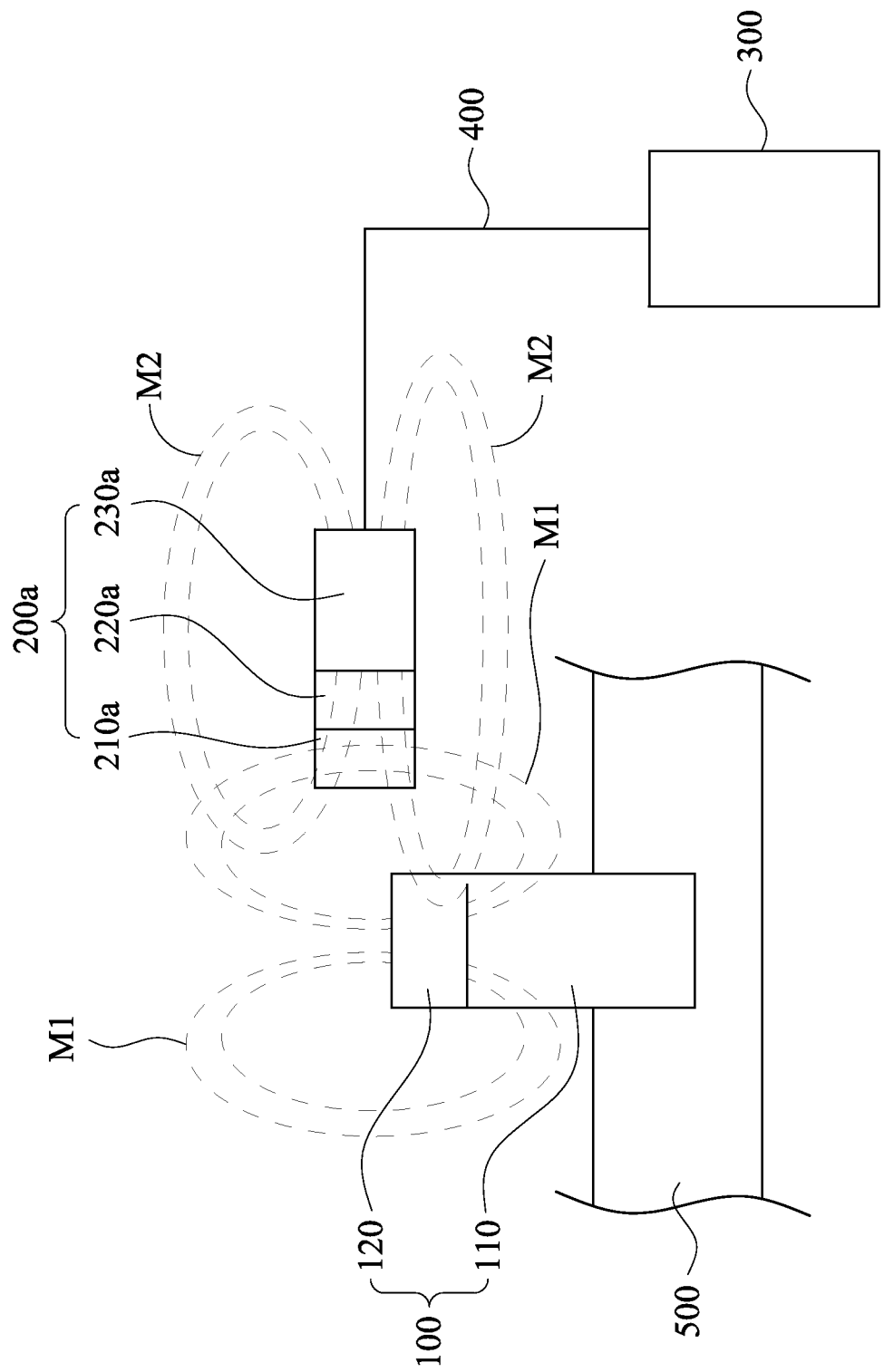
FIG. 6 is a schematic view of a system for detecting bone defects in accordance with another embodiment of the present disclosure.

FIG. 6 is a schematic view of the system for detecting bone defects in accordance with another embodiment of the present disclosure. The main difference between the embodiment and which is shown in FIG. 1 is that: in the detector 200a, the first magnetic field detecting device 210a and the second magnetic field detecting device 220a are positioned on the same end of the electromagnetic source 230a, but not on the opposite ends of the electromagnetic source 230a (See FIG. 1). In order to prevent the second magnetic field detecting device 220a from detecting the magnetic field M1 of the magnetic body 120, the second magnetic field detecting device 220a is positioned out of the range of the magnetic field M1. For example, the second magnetic field detecting device 220a can be positioned between the first magnetic field detecting device 210a and the electromagnetic source 230a, and out of the range of the magnetic field M1, so that the second magnetic field detecting device 220 can detect the variable magnetic field M2 without detecting the magnetic field M1. Other technical features in this embodiment are the same as those shown in FIG. 1 and the above related description, and thus are not described again herein.

Figure 7:
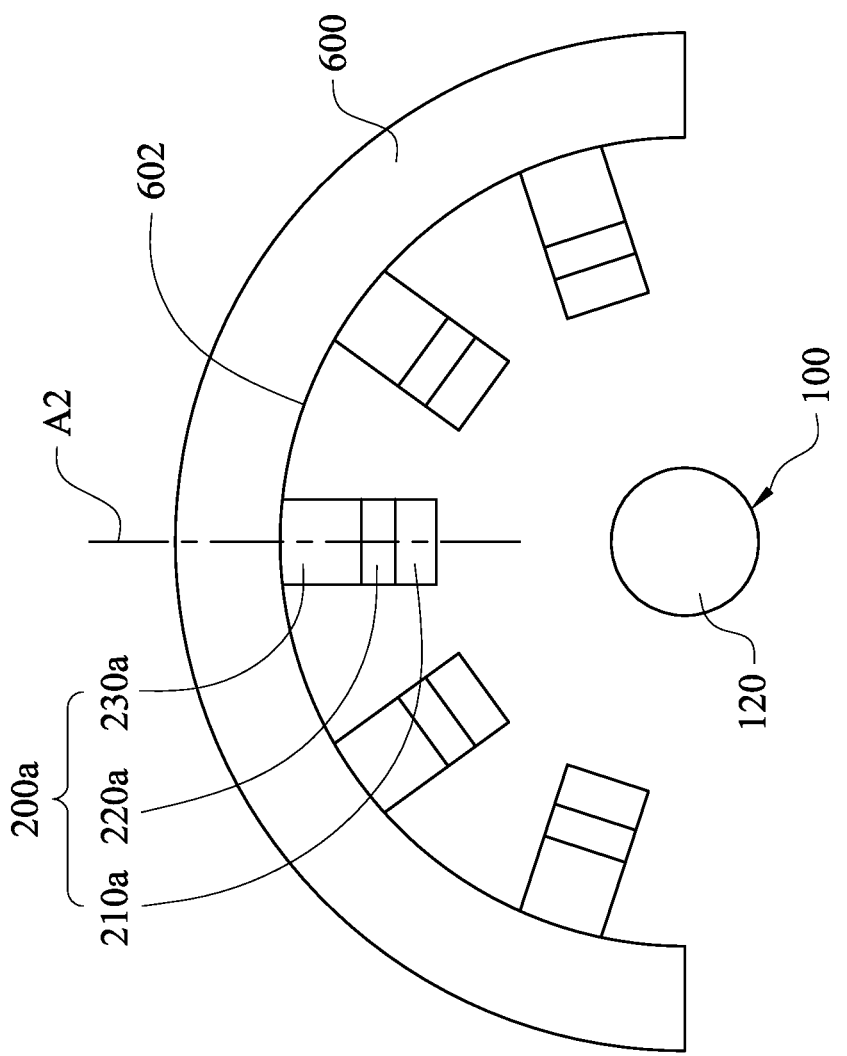
FIG. 7 is a schematic view of a system for detecting bone defects in accordance with another embodiment of the present disclosure.

FIG. 7 is a schematic view of the system for detecting bone defects in accordance with another embodiment of the present disclosure. The main difference between this embodiment and which is shown in FIG. 6 is that this embodiment has plural detector 200a. Each detector 200a has an arrangement direction A2. The first magnetic field detecting device 210a, the second magnetic field detecting device 220a and the electromagnetic source 230a are arranged along the arrangement direction A2 of the detector 200a. The arrangement directions A2 of the detectors 200a cross to each other. As a result, the detectors 200a can vibrate the dental implant contacting member 100 along different arrangement directions A2 to obtain the vibration data, thereby obtaining positions of bone defects accurately.

Figure 8:
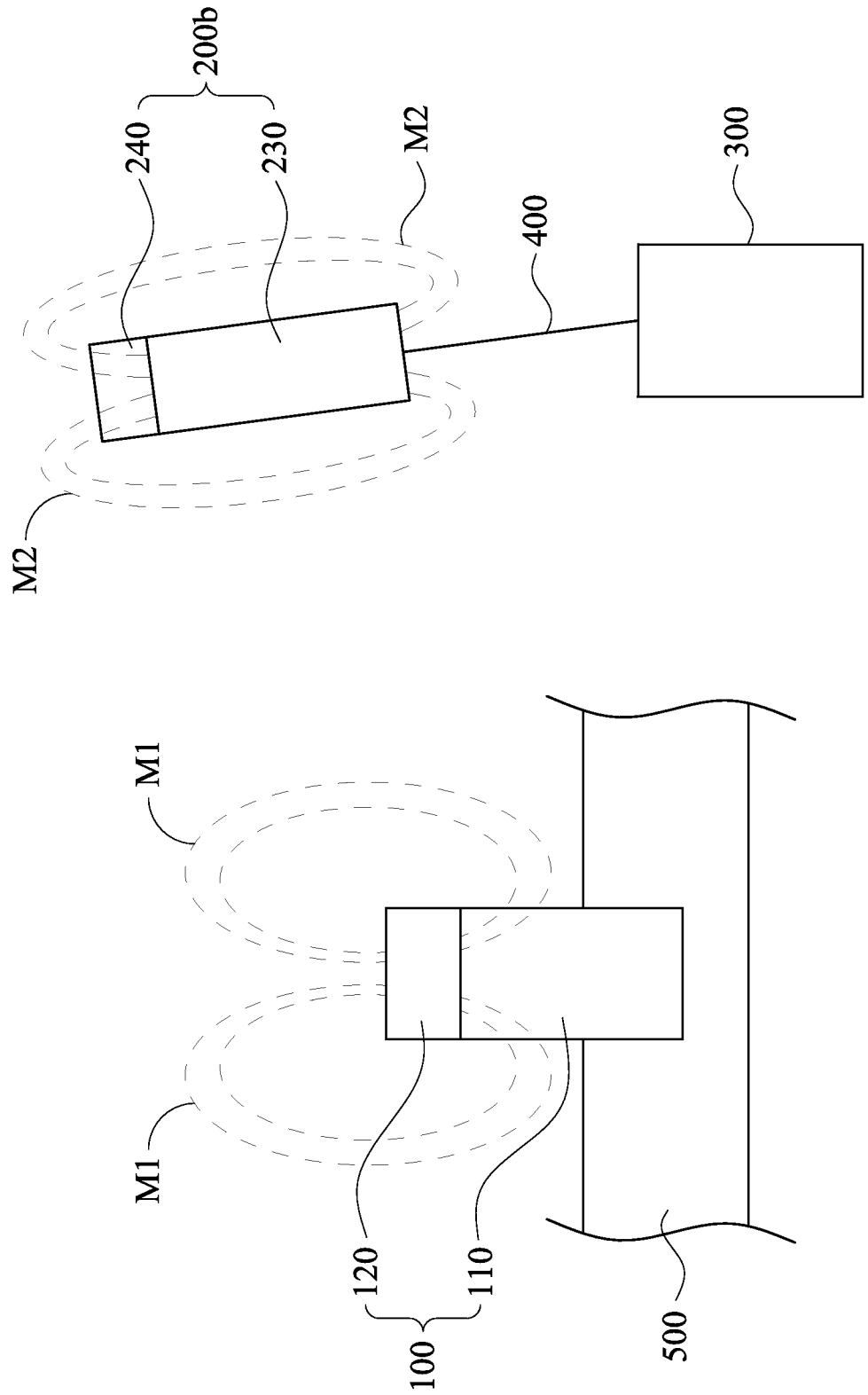
FIGS. 8 and 9 are schematic views showing a method for detecting bone defects in accordance with one embodiment of the present disclosure.
Figure 9:
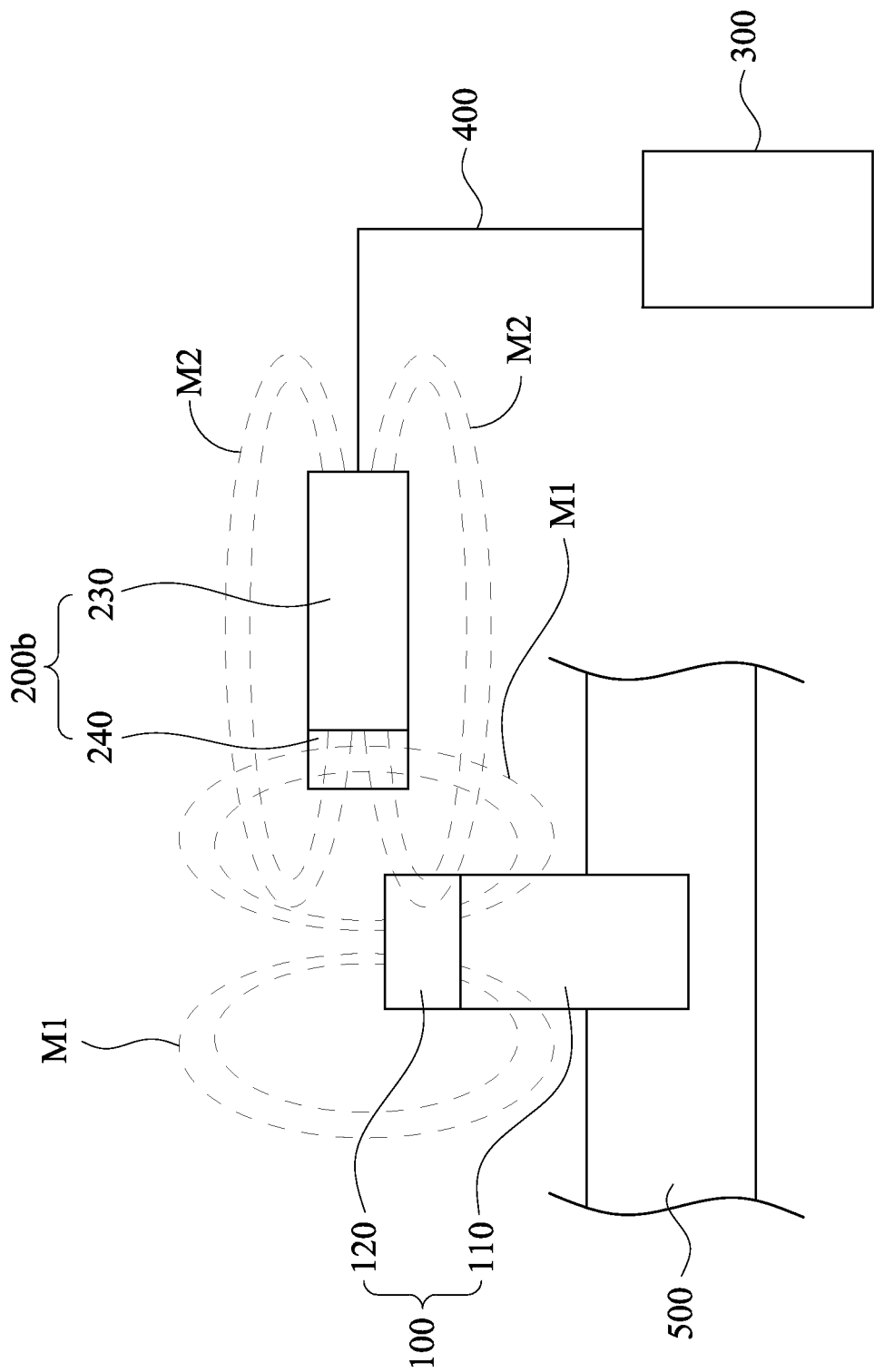

FIGS. 8 and 9 are schematic views of the method for detecting bone defects in accordance with one embodiment of the present disclosure. In this embodiment, the detector 200b includes only one magnetic field detecting device 240.

The magnetic field detecting device 240 is disposed on the electromagnetic source 230. As shown in FIG. 8, during operation, the detector 200b can be placed at an initial position at which the magnetic field detecting device 240 is positioned out of the range of the magnetic field M1 of the magnetic body 120. Then, the magnetic field detecting device 240 can detect the variable magnetic field M2 generated from the electromagnetic source 230, so as to obtain third detected data. Then, as shown in FIG. 9, the detector 200b can be moved, so that the magnetic field detecting device 240 can be moved into the magnetic field M1 of the magnetic body 120. Then, the magnetic field detecting device 240 can detect the variable magnetic field M2 and the magnetic field M1 of the magnetic body 120, so as to obtain fourth detected data. Finally, the processing device 300 can obtain the vibration data of the dental implant contacting member 100 based on the difference between the third detected data and the fourth detected data.

Because only one magnetic field detecting device 240 is required on the detector 200b, the system in this embodiment can save the cost of the magnetic field detecting device.

In this embodiment, the variable magnetic field M2 is detected alone in advance, and then, the sum of magnetic field M1 and the variable magnetic field M2 are detected. In other embodiments, the sum of the magnetic field M1 of the magnetic body 120 and the variable magnetic M2 can be detected in advance, and then, the variable magnetic field M2 can be detected alone. For example, the detector 200b can be placed at an initial position at which the magnetic field detecting device 240 is positioned in the magnetic field M1 of the magnetic body 120. Then, the magnetic field detecting device 240 can be used to detect the magnetic field M1 and the variable magnetic field M2. Then, the detector 200b can be moved, so that the magnetic field detecting device 240 can be moved out of the range of the magnetic field M1. Then, the magnetic field detecting device 240 can be used to detect the variable magnetic field M2.

The feature of obtaining the vibration data based on the third detected data and the fourth detected data is similar to that of obtaining the vibration data based on the first detected data and the second detected data, and thus is not described again herein.

Figure 10:
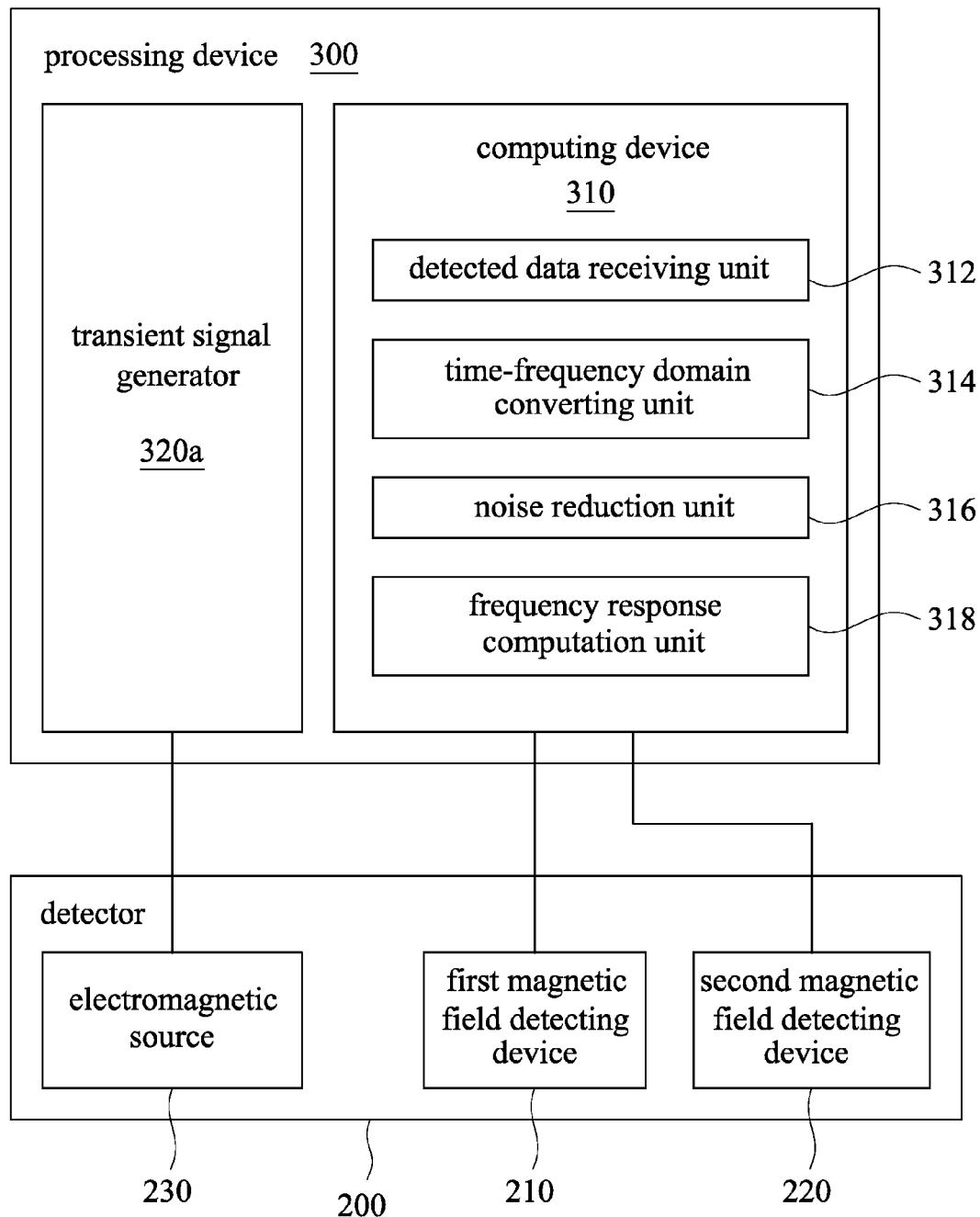
FIG. 10 is a block diagram of the system in accordance with another embodiment of the present disclosure.

FIG. 10 is a block diagram of the system in accordance with another embodiment of the present disclosure. In this embodiment, the processing device 300 includes a transient signal generator 320a. The transient signal generator 320a can be electrically connected to the electromagnetic source 230 of the detector 200, so as to control the variable magnetic field M2 by using a plurality of transient signals that have different frequencies. For example, the transient signal generator 320a provides a plurality of transient and discrete signals in form of Morlet wavelets, and the Morlet wavelets have different frequencies, so that the frequency of the variable magnetic field M2 varies with time. By using the transient signals in form of Morlet wavelets having different frequencies to control the variable magnetic field M2, the noises in the frequency-domain data generated by the time-frequency domain converting unit 314 may be reduced. Further, the transient signals may improve the vibration amplitude, which facilitates to reduce the size of the electromagnetic source 230, especially the solenoid 234 (See FIG. 4).

In some embodiments, Morlet wavelet is a wavelet that satisfies: $e^{-at^2} \times \cos(2\pi ft)$, in which t is time. The duration of the Morlet wavelet can be controlled by the exponential function, i.e. the value of a, and its frequency is decided by f.

Although the present disclosure has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present disclosure without departing from the scope or spirit of the disclosure. In view of the foregoing, it is intended that the present disclosure cover modifications and variations of this disclosure provided they fall within the scope of the following claims.

What is claimed is:

1. A system for detecting bone defects, the system comprising:
   a dental implant contacting member having a magnetic body;
   at least one electromagnetic source for generating a variable magnetic field to vibrate the magnetic body;
   at least one first magnetic field detecting device configured to detect a magnetic field of the magnetic body and the variable magnetic field, so as to generate first detected data;
   at least one second magnetic field detecting device configured to detect the variable magnetic field, so as to generate second detected data; and
   at least one computing device configured to detect bone defects based on vibration data, wherein the vibration data are obtained based on a difference between the first detected data and the second detected data.

2. The system of claim 1, wherein the second magnetic field detecting device is positioned out of a range of the magnetic field of the magnetic body.

3. The system of claim 2, wherein the first magnetic field detecting device and the second magnetic field detecting device are respectively positioned on two opposite ends of the electromagnetic source.

4. The system of claim 2, wherein the first magnetic field detecting device and the second magnetic field detecting device are positioned on the same end of the electromagnetic source.

5. The system of claim 1, further comprising:
   a frequency-sweep signal generator for controlling the variable magnetic field by using a frequency-sweep signal.

6. The system of claim 1, wherein the computing device comprises:
   a time-frequency domain converting unit, wherein the first detected data and the second detected data are time-domain data, and the time-frequency domain converting unit is used to convert the first detected data and the second detected data to first frequency-domain data and second frequency-domain data.

7. The system of claim 6, wherein the computing device comprises:
   a noise reduction unit for reducing noises in the first frequency-domain data and the second frequency-domain data.

8. The system of claim 6, wherein the computing device comprises:
   a frequency response computation unit for obtaining a frequency response function of the dental implant contacting member based on the first frequency-domain data and the second frequency-domain data, so as to obtain the vibration data comprising a vibration response.

9. The system of claim 1, wherein the first magnetic field detecting device or the second magnetic field detecting device is a Hall-effect sensor, or the first magnetic field detecting device and the second magnetic field detecting device are Hall-effect sensors.

10. The system of claim 1, further comprising:
a transient signal generator for controlling the variable magnetic field by using a plurality of transient signals that have different frequencies.

11. A method for detecting bone defects, the method comprising:
providing a detector having an electromagnetic source and at least one magnetic field detecting device disposed on the electromagnetic source;
detecting a variable magnetic field generated from the electromagnetic source by the magnetic field detecting apparatus, so as to obtain first detected data;
vibrating a magnetic body of a dental implant contacting member by the variable magnetic field;
detecting the variable magnetic field and a magnetic field of the magnetic body by the magnetic field detecting device to obtain second detected data;
obtaining vibration data based on a difference between the first detected data and the second detected data; and
detecting bone defects based on the vibration data.

12. The method of claim 11, wherein the magnetic field detecting device is positioned out of a range of the magnetic field of the magnetic body when the first detected data are obtained.

* * * * *